United States Patent [19]

Holthuis et al.

[11] Patent Number: 5,496,801
[45] Date of Patent: Mar. 5, 1996

US005496801A

[54] PARATHYROID HORMONE FORMULATION

[75] Inventors: Josephus J. M. Holthuis, AJ Leiden; Albert Mekking, CR Woerden; Alwinus A. Voetman, DT Zwanenburg, all of Netherlands

[73] Assignee: Allelix BioPharmaceuticals Inc., Ontario, Canada

[21] Appl. No.: 172,206

[22] Filed: Dec. 23, 1993

[51] Int. Cl.$^6$ ............................ A61K 37/02; A61K 37/36
[52] U.S. Cl. .................................. 514/12; 514/2; 514/970
[58] Field of Search ................................ 514/2, 12, 970

[56] References Cited

U.S. PATENT DOCUMENTS

| | | | |
|---|---|---|---|
| 3,768,177 | 10/1973 | Thomas | 273/146 |
| 4,016,314 | 4/1977 | Cowans et al. | 248/27.8 |
| 4,105,602 | 8/1978 | Colescott et al. | 514/12 |
| 4,199,060 | 4/1980 | Howard | 206/231 |
| 4,424,278 | 1/1984 | Bucovaz et al. | 436/501 |
| 4,690,952 | 9/1987 | Kagatani et al. | 514/808 |
| 4,698,328 | 10/1987 | Neer et al. | 514/12 |
| 4,812,311 | 3/1989 | Uchtman | 514/141 |
| 4,833,125 | 5/1989 | Neer | 514/12 |
| 5,059,587 | 10/1991 | Yamamoto et al. | 514/12 |

FOREIGN PATENT DOCUMENTS

| | | | |
|---|---|---|---|
| 2248550 | 4/1992 | United Kingdom | A61K 37/24 |
| WO9311786 | 6/1993 | WIPO | A61K 37/24 |

OTHER PUBLICATIONS

Charbon et al Arch Int Pharmacodyn, 1968, 171(1):3 "Diuretic and vaxcular action of parathyroid extracts in animals and man".

Hesch et al Calcif Tissue Int, 1989, 44:176 "Increase of vertebral density of combination therapy with pulsatile 1–38hPTH and sequential addition of calcitonin nasal spray in osteoporotic patients".

Hock et al Endocrinology, 1990, 127:1804 "Anabolic effect of human synthetic parathyroid hormone–(1–34) depends on growth hormone".

Hodsman et al Bone and Mineral, 1991, 14:67 "Bone densitometric and histomorphometric responses to sequential human parathyroid hormone (1–38) and salmon calcitonin in osteoporotic patients".

Hodsman et al Bone Miner, 1990, 9(2):137 "Biochemical responses to sequential human parathyroid hormone (1–38) and calcitonin in osteoporotic patients".

Hulter et al J Clin Hypertens, 1986, 2(4):360 "Chronic continuous PTH infusion results in hypertension in normal subjects".

Hulter et al Metabolism, 1984, 33(7):662 "Renal and systemic magnesium metabolism during chronic continuous PTH infusion in normal subjects".

Isaac et al Horm Metab Res, 1980, 12(9):487 "Absence of effect of 1–34 hPTH on plasma TSH, GH, FSH. LH, ACTH and cortisol in normal man".

Isaac et al J Clin Endocrinol and Metab, 1978, 47:18 "Effect of parathyroid hormone on plasma prolactin in man".

Keutman et al Current Research on Calcium Regulating Hormones, Cooper, C. W. (ed.), 1987, University of Texas Press, Austin, pp. 57–63.

Kimmel et al Endocrinology, 1993, 32(4):1577 "The Effect of recombinant human (1–84) or synthetic human (1–34) parathyroid hormone on the skeleton of adult osteopenic ovariectomized rats".

Kimura et al Biochem Biophys Res Comm, 114(2):493 "Solution synthesis of [Asn$^{76}$]–human parathyroid hormone (1–84)".

Law et al J Clin Invest, 1983, 72(3):1106 "Rapid development of renal resistance to low doses of synthetic bovine parathyroid hormone fragment 1–34".

Lawoyin et al J Clin Endocrinol Metab, 1979, 49:783 "A patient with pseudohypoparathyroidism with increased serum calcium and 1α,25–dihydroxyvitamin D after exogenous parathyroid hormone administration".

Leithner et al The Lancet, 1984, :367 "Parathyroid hormone does not inhibit platelet aggregation".

Martindale *The Extra Pharmacoepia*, The Pharmaceutical Press, London, 29th ed., 1989 at p. 1338 "Parathyroid calcitonin and biphosphonates".

Reeve et al Br Med J, 1980, 280:1340 "Anabolic effect of human parathyroid hormone fragment on trabecular bone in involutional osteoporosis: a multicentre trial".

Reeve et al Lancet, 1976, 1:1035 "Anabolic effect of low doses of a fragment of human parathyroid hormone on the skeleton in postmenopausal osteoporosis".

Reeve et al Calcif Tissue Res, 1976, 21:469 "Preliminary trial of low doses of human parathyroid hormone peptide in treatment of osteoporosis".

Reeve et al Osteoporosis Int, 1991, 1:162 "hPTH 1–34 treatment of osteoporosis with added hormone replacement therapy: biochemical, kinetic and histological responses".

Rabbani et al Endocrinology, 1988, 123:2709 "Influence of the amino–terminus on in vitro and in vivo biological activity of synthetic parathyroid hormone–like peptides of malignancy".

Rodan et al J Clin Invest, 1983, 72:1511 "Factors associated with humoral hypercalcemia of malignancy stimulate adenylate cyclase in osteoblastic cells".

Slovik et al J Bone and Mineral Res, 1986, 1(4):377 "Restoration of spinal bone in osteoporotic men by treatment with human parathyroid hormone (1–34) and 1,25–dihydroxyvitamin D".

Tsai et al J Clin Endocrinol Metab, 1989, 69(5):1024 "Bone responsiveness to parathyroid hormone in normal and osteoporotic postmenopausal women".

Vincent H. L. Lee, "Peptide and Protein Drug Delivery", published by Marcel Dekker, Inc., (N.Y.), pp. 514–516 and 538.

*Primary Examiner*—Ronald W. Griffin
*Attorney, Agent, or Firm*—Foley & Lardner

[57] ABSTRACT

Described herein are preparations containing parathyroid hormone that has been stablized with an excipient and buffering agent. Preferred preparations incorporate human PTH(1–84), mannitol as excipient and citrate as buffering agent, and are incorporated in vials as a freeze-dried powder for reconstitution to treat osteoporosis.

24 Claims, 3 Drawing Sheets

PARATHYROID HORMONE FORMULATION

FIELD OF THE INVENTION

This invention relates to pharmaceutical compositions containing parathyroid hormone. More particularly, the invention relates to parathyroid hormone formulations with improved storage stability.

BACKGROUND TO THE INVENTION

Parathyroid hormone (PTH) is a secreted, 84 amino acid product of the mammalian parathyroid gland that controls serum calcium levels through its action on various tissues, including bone. Studies in humans with certain forms of PTH have demonstrated an anabolic effect on bone, and have prompted significant interest in its use for the treatment of osteoporosis and related bone disorders.

Using the N-terminal 34 amino acids of the bovine and human hormone for example, which by all published accounts are deemed biologically equivalent to the full length hormone, it has been demonstrated in humans that parathyroid hormone enhances bone growth particularly when administered in pulsatile fashion by the sub-cutaneous and intravenous routes. A slightly different form of PTH, human PTH(1–38) has shown similar results. Because of its only recent availability, the recombinant form of the full length, human hormone, i.e., human PTH(1–84) has not yet been studied in humans although studies in rats indicate an equipotent and in some respects somewhat improved efficacy in bone growth.

PTH preparations used in these studies have been reconstituted from fresh or lyophilized hormone, and incorporate various forms of carrier, excipient and vehicle. Most are prepared in water-based vehicles such as saline, or water acidified typically with acetic acid to solubilize the hormone. The majority of reported formulations also incorporate albumin as a carrier (see for example Reeve et al, Br. Med. J., 1980, 280:6228; Reeve et al, Lancet, 1976, 1:1035; Reeve et al, Calcif Tissue Res, 1976, 21:469; Hodsman et al, Bone Miner; 1990, 9(2):137; Tsai et al, J. Clin. Endocrinol Metab, 1989, 69(5):1024; Isaac et al, Horm Metab Res, 1980, 12(9):487; Law et al, J Clin Invest, 1983, 72(3): 1106; and Hulter, J. Clin evpertens, 1986, 2(4):360). Other reported formulations have incorporated an excipient such as mannitol, which is present either with the lyophilized hormone or in the reconstitution vehicle. Formulations representative of those employed for human studies include a human PTH(1–34) preparation consisting, upon reconstitution, of mannitol, heat inactivated human serum albumin, and caproic acid (a protease inhibitor) as absorption enhancer (see Reeve et al, 1976, Calcif. Tissue Res., 21, Suppl., 469–477); a human PTH(1–38) preparation reconstituted into a saline vehicle (see Hodsman et al, 1991, 14(1), 67–83); and a bovine PTH(1–34) preparation in aqueous vehicle pH adjusted with acetic acid and containing albumin. There is also an International Reference preparation which for human PTH consists of 100 ng of hormone ampouled with 250 μg human serum albumin and 1.25 mg lactose (1981), and for bovine PTH consists of 10 μg lyophilized hormone in 0.01M acetic acid and 0.1% w/v mannitol (see Martindale, The Extra Pharmacoepia, The Pharmaceutical Press, London, 29th Edition, 1989 at p. 1338).

Commercial exploitation of parathyroid hormone requires the development of a formulation that is acceptable in terms of storage stability and ease of preparation and reconstitution. Because it is a protein and thus far more labile than the traditionally small molecular weight drugs, however, the formulating of parathyroid hormone presents challenges not commonly encountered by the pharmaceutical industry. Furthermore, and unlike other proteins that have been formulated successfully, PTH is particularly sensitive to oxidation, and further requires that its N-terminal sequence remain intact in order to preserve bioactivity.

It is an object of the present invention to provide a pharmaceutically useful PTH preparation, particularly one comprising, as active ingredient, the full length form of human PTH.

SUMMARY OF THE INVENTION

A pharmaceutically acceptable PTH preparation is now provided. According to one aspect of the present invention, the hormone preparation is in the form of a freeze dried composition, comprising a medically useful amount of parathyroid hormone, an excipient that will co-lyophilize with parathyroid hormone to form an amorphous cake, and a non-volatile buffering agent in an amount sufficient to adjust the pH of the preparation to a physiologically acceptable pH. In a preferred embodiment of the invention, the hormone in the preparation is human parathyroid hormone, the excipient is mannitol and the buffering agent is a citrate source.

According to another aspect of the present invention, there is provided a process for obtaining a PTH preparation, which comprises the steps of combining in water the PTH, the buffering agent and the excipient, and then subjecting the resulting solution to a freeze-drying process that yields a product incorporating less than 2% water by weight.

According to another aspect of the present invention, there is provided a method for obtaining a parathyroid hormone formulation for parenteral administration, which comprises the step of reconstituting a freeze-dried preparation of the present invention in sterile water.

There is further provided in accordance with the invention a therapeutically useful kit, comprising a sterile vial containing a freeze-dried preparation of the invention, a vehicle suitable for reconstitution thereof, and instructions for reconstitution, and optionally for administration. The kit may further comprise a device suitable for injection of the reconstituted preparation by the end user.

The invention is now described in greater detail and with reference to the accompanying drawings in which:

BRIEF REFERENCE TO THE DRAWINGS

FIGS. 1 and 2 show the effect of storage at 4° C. and 37° C. on the stability of PTH preparations buffered at pH 4 and pH6, where the stability is revealed by bioactivity assay (FIG. 1) and by SDS-PAGE analysis (FIG. 2).

DETAILED DESCRIPTION OF THE INVENTION

Figure 1A:
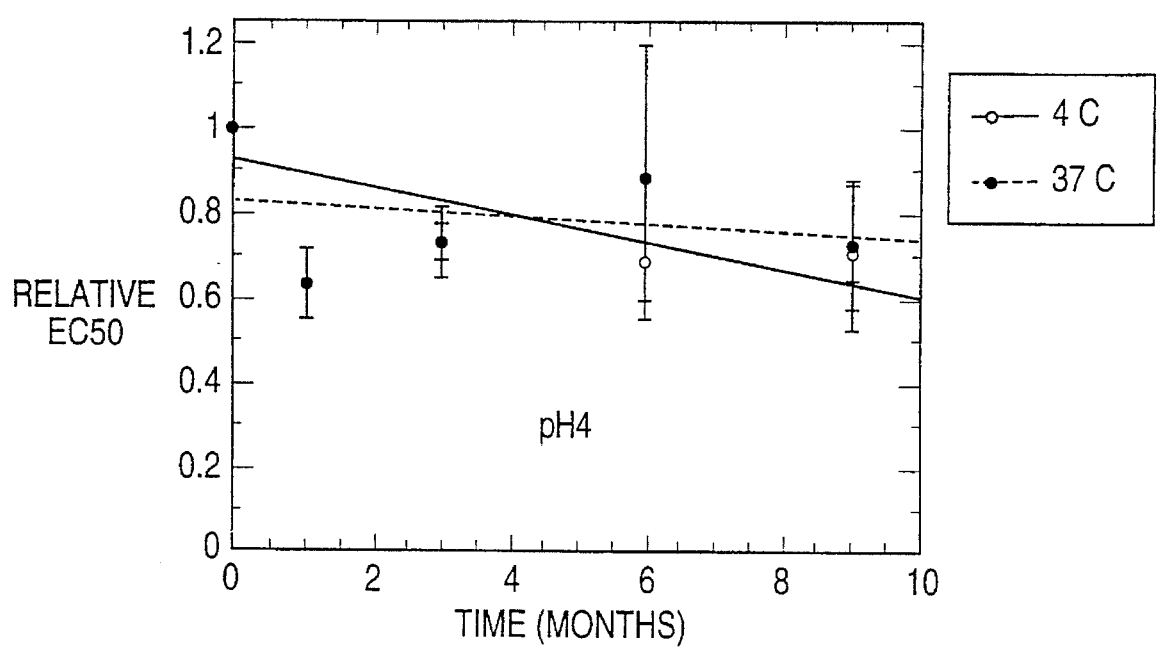

The invention relates to parathyroid hormone preparations that exhibit storage stability in terms of hormone composition and activity.

As active ingredient, the preparation desirably incorporates the full length, 84 amino acid form of human parathyroid hormone, obtained either recombinantly, by peptide synthesis or by extraction from human fluid. In this specification, the human form of PTH is abbreviated hPTH(1–84), which has the amino acid sequence reported by Kimura et al, Biochem Biophys Res Comm, 114 (2):493.

As an alternative to the full length human form of PTH, the preparation may incorporate those homologues, fragments, or variants of human PTH that have human PTH activity as determined in the ovarectomized rat model of osteoporosis reported by Kimmel et al, Endocrinology, 1993, 32(4):1577 and incorporated herein by reference.

The parathyroid hormone may for example be the bovine or porcine forms of PTH (see Keutmann et al, Current Research on Calcium Regulating Hormones, Cooper, C. W. (Ed.), 1987, University of Texas Press, Austin, pp 57–63) or fragments or variants of the mature PTH homologues. Alternatives in the form of PTH fragments incorporate at least the first 27 N-terminal residues of PTH, and desirably incorporate at least the first 34 N-terminal residues, such as PTH(1–34), PTH(1–37), PTH(1–38) and PTH(1–41). Alternatives in the form of PTH variants incorporate from 1 to 5 amino acid substitutions that improve PTH stability and half-life, such as the replacement of methionine residues at positions 8 and/or 18 with leucine or other hydrophobic amino acid that improves PTH stability against oxidation and the replacement of amino acids in the 25–27 region with trypsin-insensitive amino acids such as histidine or other amino acid that improves PTH stability against protease. These forms of PTH are embraced by the term "parathyroid hormone" as used generically herein.

The parathyroid hormone preparations of the present invention are provided in a powder form containing not more than 2% water by weight, that results from the freeze-drying of a sterile, aqueous hormone solution prepared by mixing the selected parathyroid hormone, a non-volatile buffering agent and an excipient.

The excipient incorporated in the preparation serves as a cryoprotectant during the freeze-drying process and also as a bulking agent to facilitate dosage formulation. Of the pharmaceutically acceptable excipients, the present invention avoids sugars such as lactose and maltose, and exploits only those excipients capable, when combined with the selected buffering agent, of forming a non-crystalline, amorphous cake when freeze-dried. In having selected the excipient on this basis, the cake resulting from the freeze-drying process is of the homogeneous quality desired for rapid reconstitution. Polyol-type excipients are preferred herein. An evaluation of caking properties of polyol-type excipients has revealed that mannitol is a particularly preferred excipient, not only for its ability to yield a quality cake, but also because mannitol itself confers some stability to the PTH in solution.

The buffering agent incorporated in the preparation of the present invention, in addition to being acceptable pharmaceutically, is necessarily a non-volatile buffering agent, i.e. one that is not volatilized during the freeze-drying process to the extent that pH is reduced by more than 0.4 pH units. Buffering agents used previously in PTH preparations, such as acetic acid, were found to volatilize at differential rates during the freeze-drying process, leading not only to an inconsistent product but also to the loss of buffering agent, and hence inconsistent pH levels in the reconstituted product. The non-volatile buffering agents incorporated in the present preparations are selected from those capable of buffering the preparation to a pH within a physiologically acceptable range. A pH that is physiologically acceptable is that which causes either no, or minimal, patient discomfort when the formulation is administered, and can thus vary depending on the mode of administration. For preparations that will be diluted prior to administration, such as by dissolution in a stock infusion solution, the pH of the preparation per se can vary widely, e.g., from about pH 3 to about pH 9. Where the preparation is to be administered directly after reconstitution, the PTH preparation is buffered desirably to within the pH range from 3.5 to 7.5. Suitable non-volatile buffers are accordingly those pharmaceutically acceptable agents that can buffer the pH of the preparation to within the target pH range, and include phosphate-based buffers and, preferably, citrate-based buffers such as sodium citrate/citric acid.

To provide storage stable preparations of parathyroid hormone in accordance with the invention, the selected non-volatile buffering agent is incorporated to yield a final pH within the range from 3.5 to 6.5, and the excipient is incorporated to yield a final concentration in the range from 2% to 10% (w/v). In embodiments of the invention, the pH rendered by the buffering agent is in the range from 3.8 to 6.2, and the final concentration of the excipient is from 3 to 7%, e.g. 4 to 6% (w/v). Most preferably, the buffering agent is a citrate source such as monosodium citrate/citric acid and the excipient is 5% mannitol (w/v).

The PTH preparations of the present invention incorporate PTH in a medically effective amount, a term used with reference to amounts useful either therapeutically or in medical diagnosis. The particular amount of parathyroid hormone incorporated in the preparation can be pre-determined based on the type of PTH selected and on the intended end-use of the preparation. In one application, the preparations are exploited for therapeutic purposes, and particularly for the treatment of osteoporosis. Osteoporosis therapy entails administration of the reconstituted preparation by injection, desirably sub-cutaneous injection, in unit doses that reflect the prescribed treatment regimen but are, for human PTH(1–84), within the range from 25 µg PTH/mL of injected solution to 500 µg/mL of injected solution per patient, with injection volumes being desirably from 0.3 to 1.3 mL. Accordingly, the purified and sterile-filtered PTH is desirably incorporated with the buffering agent and excipient to form an aqueous solution containing PTH in a concentration range from 25 µg/mL to 250 µg/mL, preferably 50 µg/mL to 150 µg/mL. Molar equivalents of the substantially equipotent forms of PTH, such as the PTH(1–84) variants and fragments, can be similarly incorporated in place of the human PTH(1–84), if desired.

In one embodiment of the invention, the preparations are provided in a form that yields a unit dose of 50–150 µg human PTH(1–84) upon reconstitution into about 1 mL (0.8–1.2 mL) of the reconstitution vehicle, and the vials are accordingly loaded with about 1 mL of the aqueous PTH preparation, for subsequent freeze-drying.

In a preferred embodiment of the invention, the PTH preparation subjected to freeze-drying comprises from 25 to 250 µg/mL of human PTH(1–84), from 2 to 8% by weight of mannitol, and a citrate source in an amount capable of buffering the preparation to within the range from 3.5 to 6.5 upon reconstitution in sterile water. In specific embodiments of the invention, the citrate buffering agent is incorporated in an amount sufficient to buffer the pH to 6.0±0.4.

Once the preparation is obtained as an aqueous solution containing desired amounts and concentrations of the buffering agent, excipient and PTH, individual vials are filled with the solution to the desired volume, and the vials are then subjected collectively to the freeze-drying process.

As is conventional in the art of formulation, the freeze-drying, or lyophilization, process entails a temperature cycling process that is controlled carefully to ensure that drying proceeds uniformly and to substantial completion, i.e. to yield a powder containing not more than 2% water by weight, and preferably not more than 1.5% water by weight. A protocol suitable for obtaining the present freeze-dried PTH preparations entails subjecting vials filled with the aqueous PTH preparation to a drying process having at least two different drying stages, the first being performed to drive unbound water from the aqueous preparation without causing collapse of the cake. This is achieved by first cooling the vialled aqueous PTH preparation to a product-ice temperature of lower than −30° C., preferably about −50° C., and then increasing shelf temperature to, and holding at, about −10° C. under reduced pressure of not more than 350 μbar, e.g. 260 μbar, until substantially all unbound water is driven off. Under the conditions specified in the examples herein, a drying time of 16 hours is appropriate. The second drying cycle is designed to liberate bound water from the cake, while again avoiding collapse of the cake and using a temperature below that deleterious to PTH bioactivity. This second drying step can be achieved under further reduced pressure (<50 μbar) at −10° C. for 3 hours, then warming to and holding at 25° C. until substantially all (<2%) of the bound water is driven off, e.g., for at least 12 hours but preferably for 16 hours or more. On completion, the vials can be sealed, for example by automated stoppering, and then removed from the freeze-drier and capped.

The PTH preparations of the present invention are complete in the sense that the end-user need reconstitute the preparation solely in sterile water to generate an administrable formulation. For this purpose, and in accordance with another aspect of the present invention, there is provided a medically useful kit, comprising at least one vial containing a freeze-dried PTH preparation of the invention, at least one vial containing sterile water for reconstitution of the preparation, and a sheet of instructions directing reconstitution of the freeze-dried PTH. The kit may further comprise an injection device for administration of the reconstituted formulation by the end-user. In one embodiment of the invention, the injection device is a hypodermic needle, for example a 25 gauge needle and a syringe capable of receiving a solution volume of about 0.5–5 mL, e.g. 1 or 2 mL. Alternatively, the kit may comprise a vial containing multiple doses of PTH, and a companion vial containing enough sterile water to reconstitute that multiple dose formulation.

In use, the end-user draws from the water-filled vial into the injection device, and transfers that water to the PTH-filled vial to cause mixing and reconstitution of the freeze-dried PTH powder, if necessary using the needle to draw and eject the mixture until the powder is visibly dissolved. The present PTH preparation has the advantage, however, that mixing is rapid, being complete without mixing within one minute and more usually within 30 seconds. After mixing, the end-user injects the PTH formulation in the manner and amount prescribed by the physician. In the case-where a multi-dose vial is provided, a bacteriostatic agent should be incorporated, and the formulation remaining after administration of each dose can be refrigerated for subsequent use within a time frame of several days.

In addition to their therapeutic use, the present PTH preparations can be formulated and administered to aid in medical diagnosis, and particularly to assist in establishing the diagnosis of hypoparathyroidism and pseudohypoparathyoidism in hypocalcemic patients. Except for the dose of PTH, the composition of the PTH preparation will remain as described herein for therapeutic use. An intravenously infused, single dose of human PTH(1–84) or PTH bioequivalent that is equal to 200 International Units of PTH activity is appropriate for this diagnostic purpose. Diagnosis is then made by determining the effect of administered PTH on urinary cAMP levels, with cAMP elevation being indicative of the hypoparathyroidism condition, rather than its pseudoform.

EXAMPLES

Aqueous PTH preparations were first prepared for subsequent freeze-drying by mixing human PTH(1–84), as hormone; mannitol, as excipient; and a citrate source, as buffering agent.

As a first step in generating the preparations, two aqueous admixtures were prepared from a sterile 20% (w/v) mannitol injectable solution (British Pharmacopeia). The 20% mannitol solution was blended (1) with an aqueous citric acid solution to yield a first aqueous admixture of 10 mM citric acid and 5% mannitol, and (2) with an aqueous sodium citrate monohydrate solution to yield a second aqueous admixture of 10 mM citrate and 5% mannitol. pH adjusted solutions of 5% mannitol were then obtained by blending the admixtures, in volumes appropriate to yield a 5% mannitol solution at about pH 4 (±0.2) solution and a 5% mannitol solution at about pH 6 (±0.2).

The 5% mannitol solutions (pH 4 and pH 6) then received measured amounts of freeze-dried human PTH(1–84), which was microbially produced, purified and then sterile-filtered before being freeze-dried. Measured amounts of the PTH were then added to the pH 4 and pH 6 solutions of 5% mannitol, to generate stock solutions that, when vialled at a volume of 1.1 mL, gave vials containing PTH in the following μg amounts: 100, 250, 500, 1,000 and 2,500.

For freeze-drying, solutions containing PTH at each of the prepared concentrations were aseptically filled either by hand or by an automated dispenser in 1.1 mL volumes into 5 mL glass vials (USP Type I) and then loaded in trays into a sterilized, nitrogen-purged freeze-dryer pre-cooled to −50° C. After loading, and a pre-freezing period of 4 hours, the freeze-drying chamber was evacuated by reducing pressure to 0.26 mbar for one hour. The primary drying cycle was then implemented, consisting of gradual warming over thirty minutes from −50° C. to −10° C. at which the vials were held for 16 hours. The second drying cycle was then implemented, consisting of further warming from −10° C. to 25° C. at further reduced pressure of 0.05 mbar over three hours and then holding at this temperature and pressure for 16 hours. At the end of the second drying cycle, the chamber was purged with nitrogen and brought to 0.85–0.95 bar. The tray was then raised to engage rubber stoppers in the mouths of the vials and the vial trays removed and over-capped with an aluminum seal following pressure equilibration.

Vials containing the freezed-dried PTH preparations, at various concentrations and at pH 4 or pH 6, were then stored at 4° C. and 37° C. for subsequent analysis at various time points of 1, 2, 3, 6 and 9 months. Analysis of stability was performed by reconstituting the vialed preparation into 1.1 mL of sterile water. This was achieved by injecting the water through the rubber stopper, then, after allowing up to one minute for reconstitution, removing the solution for analysis.

Figure 1B:
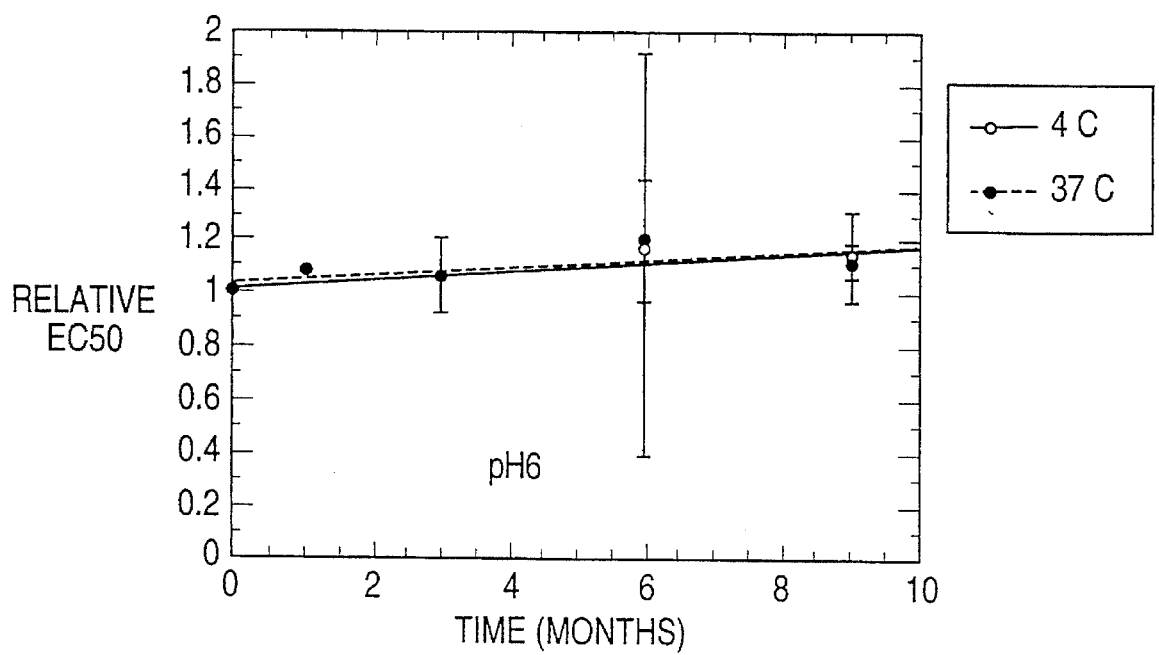
Figure 2A:
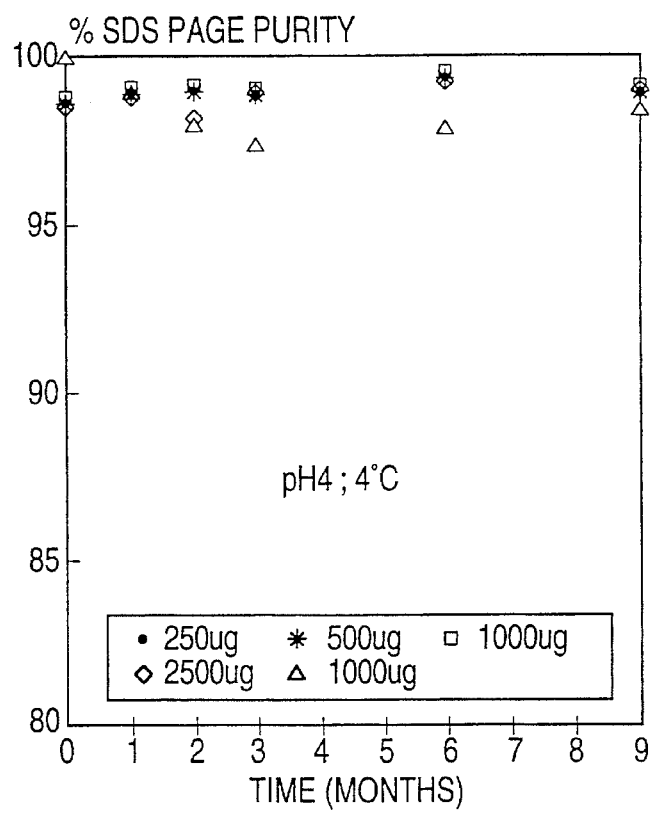
Figure 2B:
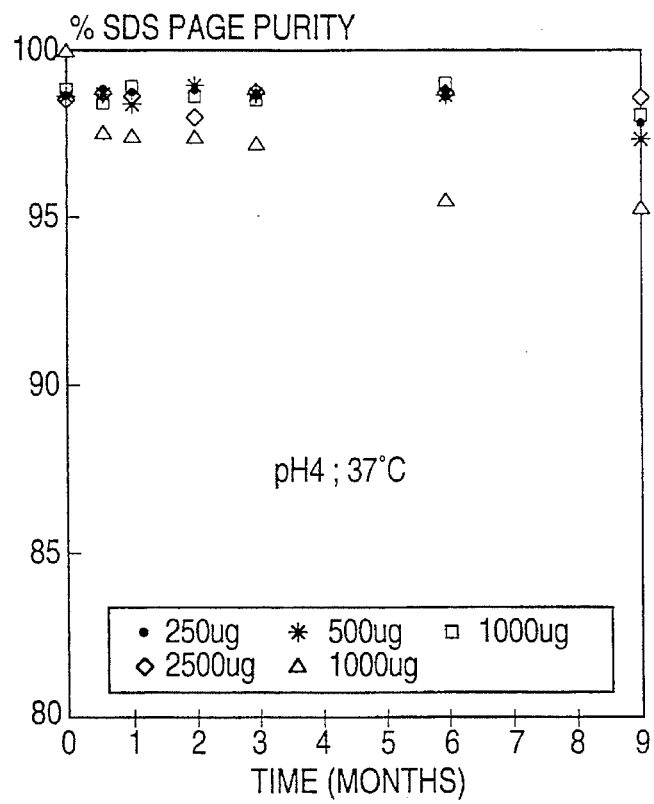
Figure 2C:
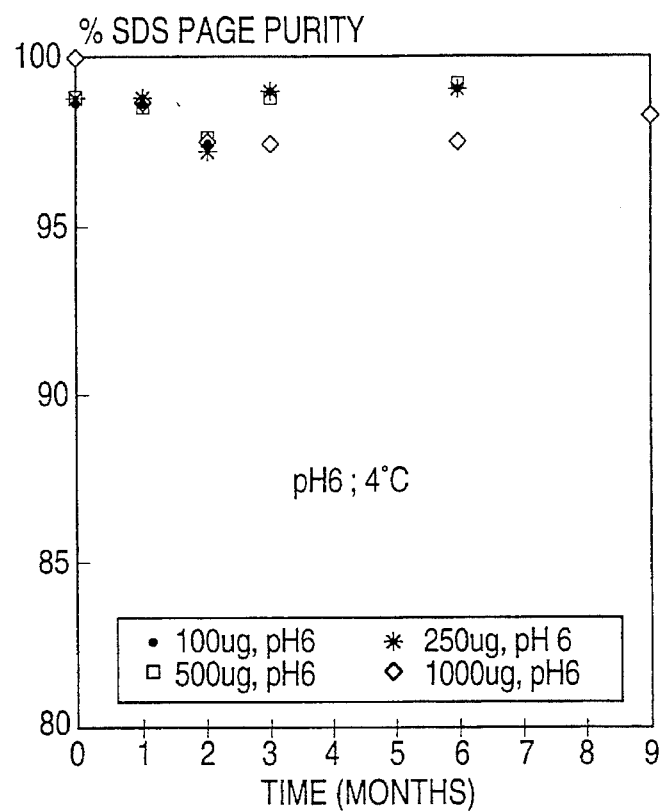
Figure 2D:
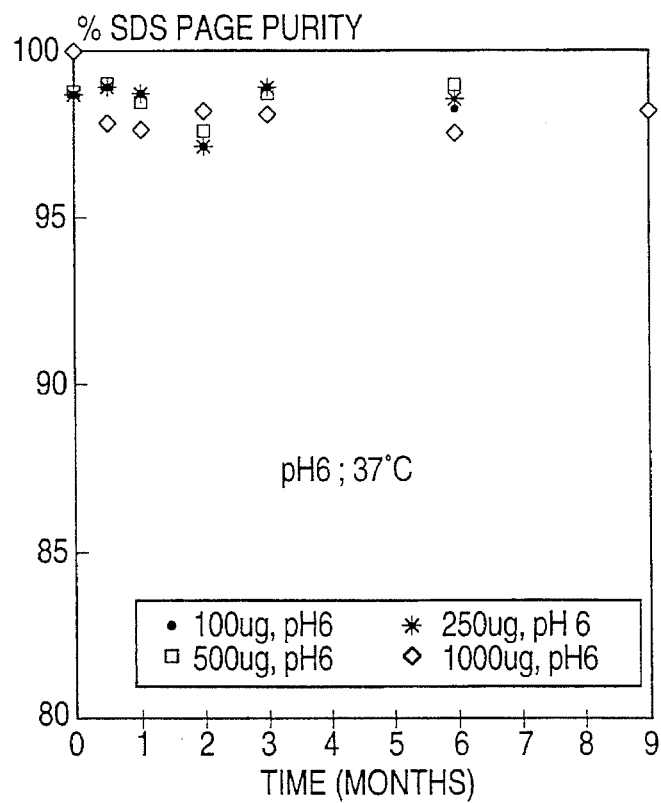

Results of the stability trials are reported below in the context of the various tests employed to evaluate the preparation:

Bioactivity of the PTH was measured using the established rat osteosarcoma cell (UMR 106)-based assay of PTH-stimulated adenylate cyclase production. Protocols for this PTH assay are reported by Rodan et al in J. Clin. Invest., 1983, 72:1511 and by Rabbani et al in Endocrinol. 1988, 123:2709. After up to nine months in storage, no significant decrease in PTH bioactivity was observed at either 4° C. or 37° C., at any PTH concentration, or at either pH 4 or pH 6. FIG. 1 illustrates, with a line of best fit between averaged results, the analytical results for a PTH preparation containing a PTH dose of 1,000 μg.

SDS-PAGE analysis of the reconstituted PTH preparations, performed in the conventional manner, similarly revealed no significant decrease of purity during storage at either pH, temperature and storage temperatures examined, as shown in FIG. 2. Some decrease in purity was revealed by RP-HPLC analysis of the reconstituted formulation, but only at the higher 37° C. storage temperature (0.7% decrease in purity per month of storage), with 4° C. storage showing no significant purity decrease by reversed phase-HPLC analysis. The stability of the intact PTH was also revealed by immunoassay (Allegro) to be constant throughout the storage period at all concentrations, pHs and temperatures evaluated.

Residual moisture in the PTH preparation was determined by the standard Karl-Fischer technique and indicated that the water content of all freeze-dried preparations remained below 2% by weight, and typically at about 1% by weight, throughout the storage period.

pH upon reconstitution revealed no significant pH alteration throughout the freeze-drying and storage process, confirming that the buffering agent had not volatilized during lyophilization. Preparations buffered to pH 4 remained at pH 4±0.2, and those buffered to pH 6 remained at pH 6±0.4.

The rate and extent of dissolution of the freeze-dried preparations were examined. All batches dissolved in 1.1 mL sterile water within one minute at room temperature. The maximum dissolution time observed was 0.5 minutes for the pH 4 preparations, and 0.4 minutes for the pH 6 preparations. Furthermore, no particles were observed upon reconstitution of the freeze-dried powder at either pH and at either storage temperature.

We claim:

1. A parathyroid hormone preparation, comprising:
   a medically useful amount of parathyroid hormone (1–84);
   a polyol excipient that co-lyophilizes with said hormone to yield an amorphous cake;
   a non-volatile buffering agent in an amount sufficient to adjust the pH of the preparation to within a physiologically acceptable pH range; and
   water.

2. A parathyroid hormone preparation according to claim 1, wherein said excipient is mannitol.

3. A parathyroid hormone formulation according to claim 1, wherein the buffering agent is a citrate source.

4. A parathyroid hormone formulation according to claim 3, wherein said excipient is mannitol.

5. A parathyroid hormone preparation according to claim 1, in the form of a freeze-dried powder containing not more than 2% water by weight.

6. A parathyroid hormone preparation according to claim 5, wherein the hormone is human PTH(1–84).

7. A parathyroid hormone preparation according to claim 6, wherein said excipient is mannitol.

8. A parathyroid hormone preparation according to claim 7, wherein the buffering agent is a citrate source.

9. A parathyroid hormone preparation according to claim 8, wherein said excipient is mannitol.

10. A parathyroid hormone preparation comprising parathyroid hormone (1–84) in a concentration within the range from 25 to 250 μg/mL;
    mannitol in a concentration in the range from 3 to 7% (w/v);
    citrate buffer in an amount sufficient to adjust the pH of the preparation to within the range from pH 3.5 to pH 6.5; and
    water.

11. A parathyroid hormone preparation according to claim 10, wherein the parathyroid hormone is human PTH(1–84).

12. A parathyroid hormone preparation according to claim 11, in the form of a freeze-dried powder containing not more than 2% water by weight.

13. A parathyroid hormone preparation according to claim 12, wherein mannitol is present in a concentration within the range from 4 to 6%.

14. A parathyroid hormone preparation according to claim 13, wherein the citrate buffer is present in an amount sufficient to adjust the pH of the preparation to pH 6±0.4.

15. A vial containing a parathyroid hormone preparation according to claim 1.

16. A vial containing a parathyroid hormone preparation according to claim 5.

17. A vial containing a parathyroid hormone preparation according to claim 9.

18. A vial containing a parathyroid hormone preparation according to claim 12.

19. A kit useful to formulate an injectable PTH solution, comprising at least one first vial containing a parathyroid hormone preparation as defined in claim 5, at least one second vial containing sterile water for reconstituting said preparation, and a sheet instructing preparation of a formulation therefrom.

20. The kit according to claim 19, further comprising a device for injection of the reconstituted PTH solution.

21. A parathyroid hormone preparation as claimed in claim 1, consisting of:
    a medically useful amount of parathyroid hormone (1–84);
    an excipient that co-lyophilizes with said hormone to yield an amorphous cake;
    a non-volatile buffering agent in an amount sufficient to adjust the pH of the preparation to within a physiologically acceptable pH range; and
    water.

22. A parathyroid hormone preparation as claimed in claim 1, consisting of:
    parathyroid hormone (1–84) in a concentration within the range from 25 to 250 μg/mL;
    mannitol in a concentration in the range from 3 to 7% (w/v);
    citrate buffer in an amount sufficient to adjust the pH of the preparation to within the range from pH 3.5 to pH 6.5; and
    water.

23. A parathyroid hormone preparation as claimed in claim 1, wherein the polyol excipient and the non-volatile buffering agent are the only substances added to render the composition stable during storage.

24. A parathyroid hormone preparation as claimed in claim 10, wherein D-mannitol and citrate buffer are the only substances added to render the composition stable during storage.

* * * * *